United States Patent [19]
Zajacek et al.

[11] 3,987,115
[45] Oct. 19, 1976

[54] PRODUCTION OF HYDROPEROXIDES

[75] Inventors: John G. Zajacek, Strafford; Francis J. Hilbert, Yeadon, both of Pa.

[73] Assignee: Atlantic Richfield Company, Los Angeles, Calif.

[22] Filed: May 29, 1975

[21] Appl. No.: 581,982

Related U.S. Application Data

[62] Division of Ser. No. 124,972, March 16, 1971, Pat. No. 3,949,003.

[52] U.S. Cl. .................... 260/631 R; 260/586 P; 260/610 B
[51] Int. Cl.² ................... C07C 27/12; C07C 27/16
[58] Field of Search .......... 260/586 P, 631 R, 610 B

[56] References Cited
UNITED STATES PATENTS

| | | | |
|---|---|---|---|
| 2,430,865 | 11/1947 | Farkes et al. | 260/610 B |
| 2,615,921 | 10/1952 | Dougherty et al. | 260/586 |
| 3,340,304 | 9/1967 | Schulz et al. | 260/631 R |
| 3,361,807 | 1/1968 | Duncanson et al. | 260/631 R |

OTHER PUBLICATIONS

Zaikov et al., Academy of Sciences of the U.S.S.R., No. 3, pp. 598–603 (1968).
Zaikov et al. (II), Izu Akad. Nauk SSSR, fer Khim, 1969(3), pp. 598–603, (Chem. Abst., vol. 71, 122842).

*Primary Examiner*—James O. Thomas, Jr.
*Assistant Examiner*—James H. Reamer
*Attorney, Agent, or Firm*—John C. Martin, Jr.

[57] ABSTRACT

Method for the production of hydroperoxides of hydrocarbons having no aliphatic or cycloaliphatic tertiary carbon atoms wherein such hydrocarbons are oxidized in the liquid phase with molecular oxygen in the presence of a tertiary alcohol and a tertiary hydroperoxide. This method gives high hydroperoxide selectivities at high conversion levels and at high conversion rates.

4 Claims, No Drawings

PRODUCTION OF HYDROPEROXIDES

This is a division of application Ser. No. 124,972 filed Mar. 16, 1971 now U.S. Pat. No. 3,949,003.

BACKGROUND OF THE INVENTION

1. Field of the Invention

This invention relates to the production of hydroperoxides of hydrocarbons having no aliphatic or cycloaliphatic tertiary carbon atoms and more particularly it relates to the production of the hydroperoxides by oxidation of such hydrocarbons in the liquid phase with molecular oxygen as the oxidizing agent.

2. Prior Art

It is well-known from the published technical and patent literature that the oxidation of hydrocarbons having tertiary carbon atoms such as isobutane, cumene, p-cymene, and the like to the corresponding hydroperoxide using molecular oxygen is commercially feasible. High selectivities at high conversions and conversion rates are readily obtainable.

The oxidation of hydrocarbons which do not have a tertiary carbon atom such as cyclohexane, ethylbenzene and the like to the corresponding hydroperoxide using molecular oxygen is not commercially feasible, since only at very low conversions and conversion rates is it possible to obtain a reasonably high selectivity for the hydroperoxide, i.e., about 50 percent.

These findings are explained by the fact that the tertiary carbon-hydrogen bond is the weakest bond in the compounds containing a tertiary compound and accordingly, this bond is attacked readily in the oxidation reaction giving a high rate of conversion and producing a tertiary hydroperoxide which is quite stable. This permits the reaction to be carried out to a high conversion level of the hydrocarbon while at the same time the selectivity to the hydroperoxide is very good. Only small amounts of acidic and high boiling residue is produced. This is not true for the oxidation of hydrocarbons having no aliphatic or cycloaliphatic tertiary carbon atoms, e.g., those having aliphatic or cycloaliphatic secondary carbon-hydrogen bonds. The rate of conversion is much slower because of the increased bond strength of the secondary carbon-hydrogen bond and the oxidation must be carried out at low conversion of the hydrocarbon to obtain high yields of the hydroperoxide, which moreover, is considerably less stable than the tertiary hydroperoxides. If it is attempted to carry out the oxidation at high conversions large amounts of high boiling residues are produced since competing side reactions occur.

The literature shows, for example, that the total conversion in the oxidation of cyclohexane cannot be above about 1.5–2 percent if a 50 percent yield of the hydroperoxide is desired. At a 4 percent conversion the maximum yield of the hydroperoxide is only about 30 percent. Heretofore, various proposals have been made to circumvent these disadvantages, for example, aluminum reactors, low rates of conversion, low total conversion of hydrocarbon alone or concurrently with the removal of by-product acids. Although these proposals have indicated that acceptable yields of hydroperoxide can be obtained by their use, none are economically or commercially feasible.

In a co-pending applicator it is proposed to add to the reaction medium stabilizers for the hydroperoxide such as tertiary butyl alcohol, water or an aqueous buffer solution. This proposal gives high selectivities for the hydroperoxide even at conversions of the hydrocarbon of 8 percent or more. This proposal which is a marked improvement over the prior art did not completely obviate all of the difficulties, since conversion rates were still relatively low, i.e., of the order of 2 percent per hour. The present invention provides an additional improvement in that relatively high conversion rates are obtainable in addition to the high conversion and selectivity. This is accomplished by introducing both a tertiary alcohol and a tertiary hydroperoxide into the reaction zone together with the hydrocarbon feed and the molecular oxygen oxidizing agent.

SUMMARY OF THE INVENTION

In accordance with this invention hydrocarbons having no aliphatic or cycloaliphatic tertiary carbon atoms such as the cycloalkanes and alkyl substituted aromatics are oxidized with molecular oxygen in the presence of a tertiary alcohol and a tertiary hydroperoxide to produce the corresponding hydroperoxide of the hydrocarbon. Temperatures in the range of 80° to 180° C. and pressures in the range of from atmospheric to 300 psi. can be employed. Reactions may be carried out either continuously or batchwise, however, in all cases good mixing, i.e., contact, should be employed.

It is an object of this invention therefore, to provide an improved method for the production of hydroperoxides of hydrocarbons having no aliphatic or cycloaliphatic tertiary carbon atoms in the molecule.

It is another object of this invention to provide a method for the production of hydroperoxides of hydrocarbons having no aliphatic or cycloaliphatic tertiary carbon atoms using molecular oxygen, wherein high hydroperoxide selectivities are obtained at high conversion levels and high rates of conversion.

It is another object of this invention to provide a method for the production of hydroperoxides of hydrocarbons having no aliphatic or cycloaliphatic tertiary carbon atoms using molecular oxygen in the presence of a tertiary alcohol and a tertiary hydroperoxide.

Other objects of this invention will be apparent from the following description of the preferred embodiments and from the claims.

DESCRIPTION OF THE PREFERRED EMBODIMENTS

The hydrocarbons which are oxidized in accordance with the method of this invention are those having aliphatic primary and secondary carbon atoms and no aliphatic tertiary carbon atoms and those having only cycloaliphatic secondary carbon atoms and no cycloaliphatic tertiary carbon atoms. Examples of the first group are ethylbenzene, n-propylbenzene, n-butylbenzene, diethylbenzene, di-n-propylbenzene and the like. Aromatic ring carbons are neither aliphatic nor cycloaliphatic and they cannot be oxidized in the manner of either secondary or tertiary aliphatic or cycloaliphatic carbons. Examples having only secondary cycloaliphatic carbon atoms are the cycloalkanes, e.g., cyclopentane, cyclohexane, cycloheptane, cyclooctane, and the like. In general, the invention has its greatest utility for the production of the hydroperoxides of hydrocarbons having from 5 to 12 carbon atoms in the molecule.

The molecular oxygen may be either in the pure form or it may be admixed with the one or more inert gases, for example $N_2$, and can be in the form of air, the important factor being that the pressure employed provides a sufficiently high concentration of oxygen in the reaction zone to give the desired reaction.

Any tertiary alcohol or tertiary hydroperoxide can be employed although tertiary butyl alcohol and tertiary butyl hydroperoxide are preferred. Other alcohols and hydroperoxides such as cumenol and cumene hydroperoxide are completely suitable and the tertiary alcohol and the tertiary hydroperoxide need not correspond to each other, thus tertiary butyl hydroperoxide and cumenol, or tertiary butyl alcohol and cumene hydroperoxide can be used.

Reaction temperatures in the range of from 80° to 180° C. are suitable, with from about 130° to 170° C. being preferred and 145° to 165° C. being the most preferred.

Pressures in the range of from atmospheric to 300 psi. can be employed, although pressures from about 100 to 250 psi. are completely satisfactory. Practically, the total pressure should be high enough to insure liquid phase at reaction temperature with the oxygen partial pressure being high enough to insure that sufficient oxygen is dissolved in the reaction mixture to provide the necessary reaction.

Mole ratios of the tertiary alcohol, such as tertiary butyl alcohol, to the hydrocarbon, such as cyclohexane, can range from 0.05:1 to 1.5:1 and mole ratios of the tertiary hydroperoxide, such as tertiary butyl hydroperoxide, to the hydrocarbon, such as cyclohexane, can range from 0.01:1 to 0.3:1. The preferred mole ratios of the alcohol to the hydrocarbon are from 0.1:1 to 1:1 and for the hydroperoxide to the hydrocarbon from 0.02:1 to 0.2:1.

In general, the hydrocarbon conversion level should not exceed about 20 mole percent and preferably should range from about 4 to 15 mole percent. The most preferred range is from 8 to 12 percent. Under these conditions a yield of at least 50 mole percent of the hydrocarbon hydroperoxide in the product is obtained which is the desired objective, although obviously a selectivity as high as possible commensurate with the conversion level and rate of conversion is most desirable.

The Examples which follow are provided to illustrate the invention in greater detail.

EXAMPLE I

A number of runs were carried out in a 1-liter autoclave. The interior of the autoclave was washed with a sodium pyrophosphate solution and then dried under vacuum. Glass-lined equipment also can be employed equally effectively. The cyclohexane was charged to the autoclave together with the tertiary butyl alcohol and the tertiary butyl hydroperoxide. The autoclave was then pressurized with pure oxygen to about 125 psig. After charging the oxygen the autoclave was heated to reaction temperature and, in general, the pressure increased to between 200 and 250 psig. As the oxidation proceeded at reaction temperature the pressure decreased. If it was desired to run the reaction to a 4 percent conversion, for example, no repressuring with oxygen was required. At conversions higher than 4 percent, one or more repressurings were required. In the first nine runs set forth in Table I, a temperature of 140° to 145° C. was employed. Runs 10, 11, 12, 13 and 14 were carried out at 150° to 155° C. while Runs 15, 16, and 17 were carried out at 160° to 165° C. The mole ratios of reactants and the product distribution in mole percent as well as the conversion level and conversion rate are shown in Table I. The reaction time is apparent, of course, from the total conversion and rate of conversion. Thus, for a total conversion of 9 mole percent and a rate of 4 percent per hour the reaction time would be 2¼ hours.

TABLE I

| Run No. | 1 | 2 | 3 | 4 | 5 | 6 | 7 | 8 |
|---|---|---|---|---|---|---|---|---|
| 1 | .126 | .037 | 71 | 11 | 9 | 8 | 4.9 | 2.9 |
| 2 | .126 | .037 | 62 | 14 | 13 | 11 | 7.1 | 2.8 |
| 3 | .126 | .075 | 71 | 14 | 7 | 8 | 4.4 | 5.0 |
| 4 | .126 | .104 | 54 | 27 | 9 | 10 | 6.2 | 8.0 |
| 5 | .227 | .067 | 64 | 12 | 12 | 11 | 9.0 | 4.0 |
| 6 | .091 | .067 | 50 | 17 | 17 | 17 | 9.6 | 4.8 |
| 7 | .565 | .173 | 40 | 17 | 15 | 28 | 18.8 | 6.5 |
| 8 | .227 | .067 | 29 | 14 | 13 | 45 | 21.3 | 6.6 |
| 9 | .453 | .067 | 57 | 7 | 14 | 22 | 12.8 | 4.3 |
| 10 | .227 | .067 | 60 | 13 | 10 | 16 | 9.8 | 9.8 |
| 11 | — | .067 | 45 | 25 | 14 | 16 | 9.6 | 13.5 |
| 12 | .912 | .067 | 46 | 19 | 12 | 23 | 10.8 | 13.2 |
| 13 | .227 | .067 | 50 | 15 | 13 | 21 | 13.0 | 13.0 |
| 14 | .227 | .067 | 52 | 12 | 10 | 24 | 12.0 | 15.3 |
| 15 | .227 | .067 | 57 | 16 | 11 | 16 | 10.6 | 22.6 |
| 16 | .912 | .067 | 76 | 0 | 10 | 13 | 8.9 | 8.4 |
| 17 | .912 | .067 | 66 | 0 | 14 | 20 | 14.1 | 8.6 |
| 18 | .293 | .086 | 56 | 20 | 11 | 13 | 8.1 | 5.8 |

Definitions of the Columns:
(1) Tertiary butyl alcohol to cyclohexane mole ratio
(2) Tertiary butyl hydroperoxide to cyclohexane mole ratio
(3) Cyclohexyl hydroperoxide mole per cent in product
(4) Cyclohexanol mole per cent in product
(5) Cyclohexanone mole per cent in product
(6) Mole per cent residue compounds in product
(7) Cyclohexane total conversion mole per cent of charge
(8) Per cent cyclohexane conversion per hour (mole per cent of charge)

Runs 1 and 2 show that if the total conversion of cyclohexane is increased, i.e., by a longer reaction time, the mole percent of cyclohexyl hydroperoxide decreases while the cyclohexanol, cyclohexanone and residue increase.

Comparing Runs 1 and 3, wherein the mole ratio of tertiary butyl hydroperoxide to cyclohexane was increased but the overall or total conversion maintained at about the same level, shows that the cyclohexyl hydroperoxide yield and other products are about unchanged as the rate of conversion per hour is increased.

Comparing Runs 3 and 4, wherein in Run 4 the mole ratio of tertiary butyl hydroperoxide to cyclohexane was further increased and at the same time the total conversion was increased, Run 4 shows a marked drop in cyclohexyl hydroperoxide yield, although the conversion per hour is increased markedly.

If Run 5 is compared with the previous runs, it will be seen that the increase in tertiary butyl alcohol to cyclohexane mole ratio allows one to increase the total conversion while the yield is comparable and the conversion per hour is about as expected from the tertiary butyl hydroperoxide to cyclohexane mole ratio.

If Runs 5 and 6 are compared it will be seen that although the total conversion and conversion per hour are about the same there is a marked drop in yield of the cyclohexyl hydroperoxide which is attributable to the lower tertiary butyl alcohol to cyclohexane mole ratio.

Run 7 compared with the previous runs demonstrates that a high mole ratio of tertiary butyl alcohol to cyclohexane and tertiary butyl hydroperoxide to cyclohexane is not sufficient to compensate for the loss in yield if the total conversion is increased.

In Run 8 similarly the yield drops very markedly when a high conversion is employed even though the mole ratios of tertiary butyl alcohol to cyclohexane and tertiary butyl hydroperoxide to cyclohexane are the same as that employed in Example 5.

Run 9 compared with Run 8 shows the effect of increasing the tertiary butyl alcohol to cyclohexane mole ratio, while lowering the total conversion since the yield of cyclohexyl hydroperoxide is essentially doubled while the conversion per hour is as expected from Runs 5 and 6.

The foregoing Runs 1 to 9 inclusive, as has been pointed out were made at a reaction temperature of 140° to 145° C. while Runs 10 to 14 inclusive, to be discussed, were carried out at 150° to 155° C.

Run 10 is comparable to Run 5 with respect to the total conversion level. It will be noted that the cyclohexyl hydroperoxide yield decreases slightly, but with the approximately 10° increase in reaction temperature, the conversion rate approximately doubled as might be expected.

In Run 11 no tertiary butyl alcohol was employed and thus the tertiary butyl hydroperoxide had a marked effect on increasing the rate of conversion, but at the expense of a marked decrease in cyclohexyl hydroperoxide yield, and a corresponding increase in the cyclohexanol and cyclohexanone production.

In Run 12 an attempt was made to increase the conversion slightly over that in Run 11 and at the same time try to improve the cyclohexyl hydroperoxide yield by utilizing a high tertiary butyl alcohol to cyclohexane mole ratio. It will be obvious that too much alcohol was employed since the yield did not improve while the residue increased.

In Run 13 the more optimum mole ratios of tertiary butyl alcohol to cyclohexane and tertiary butyl hydroperoxide to cyclohexane utilized in Run 5 were employed although the cyclohexyl hydroperoxide yield dropped from 64 to 50. The conversion was increased from 9 to 13 and the rate of conversion was increased from 4 to 13.

Run 14 was similar to Run 13 except that a slightly lower conversion was employed but with essentially no change in products by a small increase in conversion per hour. These differences however, are not considered significant.

In general, Runs 10 to 14 show that by utilizing the same mole ratios of tertiary butyl alcohol to cyclohexane and tertiary butyl hydroperoxide to cyclohexane as were employed in the lower temperature runs, and by carrying out the reaction to the same conversion level that essentially the same product yields can be expected with the only difference being an increased reaction level as might be expected from the increased reaction temperature.

Runs 15, 16, and 17 were carried out at a still higher temperature level, i.e., 160° to 165° C.

Run 15 is comparable to Run 10 and Run 5, although it was carried out to a slightly higher conversion level, thereby causing a decrease in cyclohexyl hydroperoxide yield. It will be noted that the rate of conversion is essentially double that for Run 10 which in turn is essentially double that of Run 5 as would be expected from a 10° reaction temperature increase.

Runs 16 and 17 show an interesting comparison with Run 12 in that at the higher temperatures the high tertiary butyl alcohol to cyclohexane mole ratio is advantageous by permitting an increase in total conversion while giving a marked increase in cyclohexyl hydroperoxide yield. The rate, however, is decreased somewhat because of the high alcohol to cyclohexane mole ratio. Run 16 is particularly important since it shows the highest yield with both a high total conversion and rate of conversion.

Runs were carried out comparable to Runs 10 and 11, i.e., at 150° to 155° C. In one of these runs no tertiary butyl hydroperoxide or tertiary butyl alcohol was employed and at a conversion level of about 8 percent, the rate was only 2 percent per hour and the cyclohexyl hydroperoxide yield was only 22 percent. When tertiary butyl alcohol was employed in this same reaction, but no tertiary butyl hydroperoxide, at a conversion level of about 8 percent the conversion rate was still only about 2 percent but the yield of cyclohexyl hydroperoxide increased to about 50 percent. It will be seen from a comparison of these data with Runs 10 and 11, that the presence of both the tertiary butyl alcohol and the tertiary butyl hydroperoxide is required to provide a high yield at a high conversion level with a high conversion rate.

EXAMPLE II

A run was carried out in exactly the same manner as Run 10, except that the tertiary alcohol was cumenol and the tertiary hydroperoxide was cumene hydroperoxide. The mole ratio of cumenol to cyclohexane was 0.329:1 and the mole ratio of cumene hydroperoxide to cyclohexane was 0.086:1. A cyclohexyl hydroperoxide yield of 56 mole percent, a cyclohexanol yield of 20 mole percent, a cyclohexanone yield of 11 mole percent and a residue of 13 mole percent was obtained at a conversion level of 8.1 mole percent and a percent conversion rate of 5.8 percent per hour. This run demonstrates that other tertiary alcohols and hydroperoxides are effective in the process of this invention.

EXAMPLE III

In order to show the effectiveness of the combination of tertiary butyl alcohol and tertiary butyl hydroperoxide in the oxidation of ethylbenzene, two batch runs were made in a 1-liter stirred autoclave, by passing air continuously into the autoclave at 100 psig. under pressure control, agitation was constant at 2000 rpm. a temperature of 150° C. was utilized in both runs. The feed composition and results obtained are shown in Table II.

TABLE II

| Run No. | 1 | 2 | 3 | 4 |
|---|---|---|---|---|
| 1 | 0.16 | 0.001 | 5½ | 74 |
| 2 | 0.17 | 0.07 | 3½ | 74 |

Definition of Columns:
(1) Tertiary butyl alcohol to ethylbenzene mole ratio
(2) Tertiary butyl hydroperoxide to ethylbenzene mole ratio
(3) Time required to reach 20 mole per cent conversion of ethylbenzene, hours
(4) Ethylbenzene hydroperoxide mole per cent in product at 20 mole per cent conversion of ethylbenzene These results show that in Run 1 the mole ratio of tertiary butyl hydroperoxide to ethylbenzene was too small since the desired rate improvement was not obtained. Run 2 shows that by increasing the mole ratio of tertiary butyl hydroperoxide to ethylbenzene into the desired range that the time to reach the desired conversion is decreased by about 40 percent.

From the foregoing examples it will be seen that by carrying out the method of this invention in the substantial absence of metal ions which catalyze the decomposition of the hydroperoxide, this oxidation method, therefore, is non-catalytic with respect to the presence of metal ions, in particular, heavy metal ions and thus, provides a high selectivity for the hydroperoxide product while minimizing the by-product alcohol, ketone, acids, and others. The oxidate, accordingly, can be used directly as the oxidizing agent in the epoxidation of olefins in the presence of a molybdenum catalyst. In the epoxidation reaction the hydroperoxide is reduced to the alcohol which can be recovered along with any by-product alcohol originally produced when the hydroperoxide was produced.

An additional advantage is that the tertiary alcohol-tertiary hydroperoxide compounds needed for the method of this invention are available commercially.

We claim:

1. A method for the oxidation of cyclohexane to produce a mixture of oxidation products comprising cyclohexyl hydroperoxide, cyclohexanol, and cyclohexanone, wherein the yield of cyclohexyl hydroperoxide in the oxidation products is at least 50 mole percent, comprising contacting said cyclohexane in the liquid phase with molecular oxygen at a temperature in the range of from 80° to 180° C. in the presence of a tertiary alcohol selected from the group consisting of tertiary butyl alcohol and cumenol and a tertiary hydroperoxide selected from the group consisting of tertiary butyl hydroperoxide and cumene hydroperoxide, the mole ratio of said alcohol to said cyclohexane being in the range of from 0.05:1 to 1.5:1, the mole ratio of said hydroperoxide to said cyclohexane being in the range of from 0.01:1 to 0.3:1.

2. The method of claim 1 wherein said tertiary alcohol is tertiary butyl alcohol and said tertiary hydroperoxide is tertiary butyl hydroperoxide.

3. The method of claim 1 wherein said cyclohexyl hydroperoxide is subsequently reduced to cyclohexanol.

4. The method of claim 3 wherein cyclohexanol is recovered from the reaction mixture.

* * * * *